United States Patent
Dilk et al.

(10) Patent No.: US 6,252,120 B1
(45) Date of Patent: Jun. 26, 2001

(54) PROCESS FOR THE PREPARATION OF 2,4,4, 7-TETRAMETHYL-OCT-6-EN-3-ONE AND ITS USE AS AN AROMA SUBSTANCE

(75) Inventors: Erich Dilk; Peter Wörner, both of Holzminden (DE)

(73) Assignee: Haarmann & Reimer GmbH, Holzminden (DE)

( * ) Notice: Subject to any disclaimer, the term of this patent is extended or adjusted under 35 U.S.C. 154(b) by 0 days.

(21) Appl. No.: 08/728,009

(22) Filed: Oct. 9, 1996

(30) Foreign Application Priority Data

Oct. 16, 1995 (DE) .............................. 195 39 625

(51) Int. Cl.$^7$ .................................. C07C 45/00
(52) U.S. Cl. .............................. 568/393; 512/27
(58) Field of Search ................ 568/393; 512/27

(56) References Cited

U.S. PATENT DOCUMENTS

| | | | |
|---|---|---|---|
| 3,453,317 | * 7/1969 | Marbet et al. | 568/393 |
| 3,668,255 | 6/1972 | Meuly et al. | 568/393 |
| 3,983,175 | * 9/1976 | Tamai et al. | 568/393 |
| 4,385,185 | * 5/1983 | Gebauer et al. | 512/27 |
| 4,426,321 | * 1/1984 | Ochsner | 512/27 |
| 4,544,714 | * 10/1985 | Ochner | 512/23 |
| 4,686,291 | * 8/1987 | Lantzsch et al. | 568/393 |

OTHER PUBLICATIONS

M.T. Reetz, et al., Lewis Acid Mediated α–Alkylation of Ketones Using $S_N1$ Reactive Alkylating Agents, Tetrahedron Letters, No. 51, pp. 4971–4974, (1979).

Babayan, Zhur Obshschei Khim, 24.

Chemical Abstracts, vol. 49.

E.V. Dehmlow, et al., Phase Transfer Catalysis, VCH Publishers, New York, 1993, Third, Revised and Enlarged Edition.

Chemical Abstracts, vol. 49, No. 1, 1955, Columbus, Ohio, US; abstract No. 10879, XP002021344 *Zusammenfassung*, & Zhur. Obshchei. Khim., Bd. 24, 1954, Seiten 1887–1893, A.T. Babayan, et al., "Alkylation in aqueous medium in the presence of quaternary ammonium salts".

Tetrahedron Letters, Bd. 51, 1979, Seiten 4971–4974, XP002021343, M.T. Reetz et al., "Lewis acid mediated alpha–alkylation of ketones using SN–1 reactive alkylating agents", *das ganze Dokument*.

* cited by examiner

Primary Examiner—James H. Reamer
(74) Attorney, Agent, or Firm—Norris McLaughlin & Marcus

(57) ABSTRACT

2,4,4,7-Tetramethyl-oct-6-en-3-one, as a perfume component, imparts new smell facets to perfume compositions. It can be prepared in a good yield by prenylation of 1-chloro-3-methyl-2-butene in a 2-phase process.

6 Claims, No Drawings

PROCESS FOR THE PREPARATION OF 2,4,4,7-TETRAMETHYL-OCT-6-EN-3-ONE AND ITS USE AS AN AROMA SUBSTANCE

The invention relates to the use of 2,4,4,7-tetramethyl-oct6-en-3-one ("TMO" below) for the preparation of aroma substance compositions, and to a two-phase process for its preparation.

It is known from U.S. Pat. No. 3,668,255 that open-chain branched olefinically unsaturated compounds have a pleasant smell, so that they are suitable for formulation of perfumes and perfume bases. One of the compounds mentioned therein is TMO.

TMO can be prepared by alkylation of the silenol ether of diisopropyl ketone with prenyl chloride (=1-chloro-3-methyl-2-butene), according to M. T. Reetz et al. (Tetrahedron Letters 51, (1979) 4971), or by prenylation of diisopropyl ketone using a solid alkali metal hydroxide in the presence of ammonia or an amine, in accordance with U.S. Pat. No. 3,668,255.

However, U.S. Pat. No. 3,668,255 does not contain concrete instructions for the preparation of TMO. When the generally recommended reaction conditions are applied to the preparation of TMO, it is then found that TMO is formed only in traces. We have been unable to ascertain the reason for this; however, it is striking that the starting compound diisopropyl ketone is not mentioned in U.S. Pat. No. 3,668,255, although the list of ketones is very extensive. Under closer consideration, nevertheless, it is striking that only those ketones which have no branching site in at least one α-position are recommended as starting components. The authors have possibly already recognized themselves that the process recommended cannot be applied to all desired ketones with success.

Surprisingly, it has now been found that the prenylation of diisopropyl ketone leads to good yields of TMO if the reaction is carried out in the presence of an aqueous phase and a phase transfer catalyst.

The invention thus relates to a process for the preparation of 2,4,4,7-tetramethyl-oct6-en- 3-one by reaction of diisopropyl ketone and 1-chloro-3-methyl-2-butene, characterized in that the reaction is carried out in a 2-phase system comprising an aqueous phase in the presence of a phase transfer catalyst.

The diisopropyl ketone can be employed in amounts of 0.5 to 10, preferably 0.8 to 2 mol per mol of prenyl chloride.

The phase transfer catalysts for the process according to the invention include phosphonium, sulphonium and— preferably—ammonium compounds. Preferred ammonium compounds correspond to the formula (I)

$$R^1R^2R^3R^4\ N^\oplus X^\ominus \qquad (I)$$

wherein

R$^1$ to R$^4$ independently of one another denote C$_1$–C$_{18}$-alkyl or benzyl and X$^\ominus$ denotes iodide, bromide, chloride, hydroxide or hydrogen sulphate.

Preferred compounds (I) include, in particular, the tetrabutyl ammonium salts.

The compounds (I) can be used in amounts of 0.1 to 10, preferably 1 to 5, mol %, based on the starting compound employed in a deficit.

The reaction is in general carried out in the presence of a base. Suitable bases are, above all, the alkali metal hydroxides, such as sodium hydroxide and potassium hydroxide. Preferred amounts are 1 to 10 mol per mole of prenyl chloride. According to a preferred embodiment, the aqueous phase comprises a saturated solution of an alkali metal hydroxide.

The reaction can be carried out with or without organic water-immiscible solvents; water-miscible organic solvents, such as methanol, ethanol, acetone and the like, are preferably omitted. Suitable organic solvents include, for example, aliphatic hydrocarbons, such as petroleum ether, cycloaliphatic hydrocarbons, such as cyclohexane, and aromatics, such as benzene, toluene and xylene. If such solvents are used, the amount can be 50 to 300, preferably 80 to 200%, by weight, based on the sum of the starting components.

The aqueous phase can vary within wide ranges of amounts. Preferred amounts are 80 to 500, preferably 100 to 300% by weight, based on the sum of the starting components.

The process according to the invention can be carried out at temperatures between 20 and 90° C., preferably at 30 to 80° C. The reaction times can be 1 to 25 hours, preferably 4 to 16 hours.

For working up, the phases can be separated and the reaction product can be isolated from the organic phase, for example by distillation, if appropriate under reduced pressure.

The process according to the invention gives TMO in good yields. This is all the more astonishing, since according to U.S. Pat. No. 3,668,255, anhydrous conditions are preferred (column 5, lines 47 to 50). It thus seems as though a process analogous to the proposal by Babayan et al., Zhur Obshschei Khim 24 (1954), 1887; Chem. Abst. 49 (1955), 10 879 precisely with diisopropyl ketone proceeds very satisfactorily for the preparation of TMO, although the authors of U.S. Pat. No. 3,668,255 evidently found serious disadvantages for the starting ketones used by them.

TMO can readily be combined with other aroma substances to give novel interesting compositions, the amount of TMO preferably being 1 to 50% by weight, based on the total composition. Surprisingly, it has been found that the smell aspects of TMO emerge to an increased extent or contribute to new smell facets, in particular in combination with other aroma substance materials.

Thus, tetramethyloctenone is distinguished by a specific action in the tart-fresh fragrance range. Smell impressions from the fragrance field of bergamot, grapefruit and oil of clary sage are caused here in particular.

It is therefore outstandingly suitable for fragrance compositions such as, for example, a) tart eau de toilette notes in which the TMO imparts a bitter bergamot impression extending to the strikingly tart-male fragrance impression of oil of clary sage, b) grapefruity cosmetic fragrances in which TMO causes interesting fresh effects in the overhead note and imparts impact, c) imitations of essential oils, where it excellenty underlines the character of oil of clary sage.

The invention therefore also relates to the use of TMO in perfume compositions which have a tart-fresh character.

Apart from in fine perfumery, such compositions can be used for perfuming cosmetics, such as creams, lotions, aerosols and toilet soaps, and industrial articles, such as cleaning compositions and detergents, softening rinses, disinfectants and textile treatment compositions.

The percentage data of the following examples relate to the weight, unless stated otherwise.

EXAMPLES

Example 1

2,4,4,7-Tetramethyl-oct-6en-3-one 2400 g of sodium hydroxide solution (50% strength), 40 g of tetrabutylammonium bromide and 548 g of diisopropyl ketone are initially introduced into a 4 l double-walled vessel and heated to 30° C. 418 g of prenyl chloride are metered in over a period of 1 hour, while stirring, and the mixture is then subsequently stirred for 16 hours. 1200 g of water are added, the mixture is stirred for 20 minutes and the phases are then separated. 895 g of an organic phase, which is distilled over a 60 cm packed column, are obtained.

437 g (60% of theory, based on the prenyl chloride employed) of product, boiling point$_{10mbar}$=112° C., are obtained.

Smell: grapefruit, vetiver, oil of clary sage, bergamot, good impact

Use

Use Example 1

|  | A Parts by weight | B Parts by weight |
|---|---|---|
| Bergamou Identoil farblos ® H + R | 175 | 175 |
| Dihydromyrcanol | 200 | 200 |
| Lemon oil | 100 | 100 |
| Vertocitral ® H + R | 5 | 5 |
| Methyldihydrojasmonat ® Firmenich | 50 | 50 |
| Citrophoral Supra ® H + R | 5 | 5 |
| Lavandin oil Grosso | 25 | 25 |
| French oil of clary sage | 10 | 10 |
| Geranium Chin. Synthessence ® H + R | 30 | 30 |
| Damascon Betra ® Firmenich | 1 | 1 |
| Precyclemone B ® IFF | 19 | 19 |
| Isocyanat ® H + R | 15 | 15 |
| Sandolene H + R | 5 | 5 |
| Cedryl ketone | 100 | 100 |
| Chromanolid 50% in DEP ® H + R | 100 | 100 |
| Evernyl ® Givaudan-Roure | 10 | 10 |
| Ambroxid Rein ® H + R | 10 | 10 |
| Dipropylene glycol | 140 | 100 |
| 2,4,4,7-Tetramethyl-oct-6-en-3-one | — | 40 |

The addition of tetramethyloctenone causes an unmistakable fresh-green peak in the overhead note of the tart man's composition.

Use Example 2

|  | A Parts by weight | B Parts by weight |
|---|---|---|
| Aldehyde C10 | 2.0 | 2.0 |
| Aldehyde C11 undecylene | 1.0 | 1.0 |
| Aldehyde C12 MNA | 2.0 | 2.0 |
| Vertocitral ® H + R | 5.0 | 5.0 |
| Isoananat ® H + R | 5.0 | 5.0 |
| Dihydromyrcenol ® IFF | 75.0 | 75.0 |
| Terpinyl acetate | 50.0 | 50.0 |
| Citral IFRA ® H + R | 18.0 | 18.0 |
| Geranitril ® BASF | 5.0 | 5.0 |
| Orange oil Weiss | 120.0 | 120.0 |
| Lavandin oil Grosso | 20.0 | 20.0 |
| American curled mint oil | 2.0 | 2.0 |
| Isobornyl acetate | 40.0 | 40.0 |
| Borneol L | 5.0 | 5.0 |
| Hydroxybenzylacetone Para | 1.0 | 1.0 |
| Lilial | 5.0 | 5.0 |
| Lyral ® IFF | 10.0 | 10.0 |
| Linalool | 50.0 | 50.0 |
| Dimethylbenzylcarbinyl butyrate | 2.0 | 2.0 |
| Rosenoxid Rac. ® Dragoco | 1.0 | 1.0 |
| Damascon Alpha 10% DEP ® Firmenich | 3.0 | 3.0 |
| Benzyl acetate | 10.0 | 10.0 |
| Jasmin 151 ® H + R | 5.0 | 5.0 |
| Benzyl salicylate | 124.0 | 124.0 |
| Hexyl salicylate | 30.0 | 30.0 |
| Anethol NPU 21/22 degrees C | 2.0 | 2.0 |
| Coumarin | 5.0 | 5.0 |
| Cedrenylacetat IFF ® IFF | 15.0 | 15.0 |
| Patchoulyoel Entf. H + R ® H + R | 10.0 | 10.0 |
| Piconia ® IFF | 10.0 | 10.0 |
| Sandel H + R ® H + R | 5.0 | 5.0 |
| Evernyl ® Givaudan-Roure | 5.0 | 5.0 |
| Russia leather oil pale 10% DEP | 2.0 | 2.0 |
| Coumin-aldehyde | 2.0 | 2.0 |
| Ambroxid 30% in Hercolyn 10% DEP ® H + R | 3.0 | 3.0 |
| Niso-Salicylat 38/62 ® H + R | 20.0 | 20.0 |
| DEP | 30 | — |
| 2,4,4,7-Tetramethyl-oct-6-en-3-one | — | 30 |

DEP=diethyl phthalate

After addition of 2,4,4,7-tetramethyl-oct-6-en-3-one, the mixture smells more vividly fresh with a clear peak of grapefruit.

Use Example 3

|  | A/Parts by weight | B/Parts by weight |
|---|---|---|
| Nonal | 1.0 | 1.0 |
| Undecanol | 1.0 | 1.0 |
| Linalyl acetate | 645.0 | 645.0 |
| Linalyl isobutyrate | 20.0 | 20.0 |
| Terpinyl acetate Alpha L | 5.0 | 5.0 |
| Terpinolene | 2.0 | 2.0 |
| Pinene Beta Supra | 8.0 | 8.0 |
| Limonene L-80 degrees | 10.0 | 10.0 |
| Pinene Alpha Supra | 4.0 | 4.0 |
| Ocimene | 3.0 | 3.0 |
| Eucalyptol | 2.0 | 2.0 |
| Cymol Para Supra | 6.0 | 6.0 |
| Bornyl acetate L cryst. | 2.0 | 2.0 |
| Camphene L Supra | 2.0 | 2.0 |
| Nerolidol | 5.0 | 5.0 |
| Linalool oxide | 3.0 | 3.0 |
| Linalool | 80.0 | 80.0 |
| Terpineol Alpha L cryst. | 10.0 | 10.0 |
| Nerol Supra | 20.0 | 20.0 |
| Geraniol Supra | 40.0 | 40.0 |
| Geranyl acetate Supra | 20.0 | 20.0 |
| Geranyl isobutyrate | 10.0 | 10.0 |
| Neryl acetate Supra | 10.0 | 10.0 |
| Nonadienal/A in TEC | 1.0 | 1.0 |
| Caryophyllene rect. | 30.0 | 30.0 |
| Flouve oil | 1.0 | 1.0 |
| Oil of clary sage abs. | 7.0 | 7.0 |
| Liatrix abs. incol. Maximarome | 1.0 | 1.0 |
| Ambroxid Rein ® (H + R) | 1.0 | 1.0 |
| Triethyl citrate 1.0 | 50.0 | — |
| 2,4,4,7-Tetramethyl-oct-6-en-3-one | — | 50.0 |

Replacing triethyl citrate by 2,4,4,7-tetramethyl-oct-6-en-3-one significantly improves the impression of true oil of clary sage to an extent which was not to be expected by the addition of 5%.

What is claimed is:
1. Process for the preparation of 2,4,4,7-tetramethyl-oct-6-en-3-one by reaction of diisopropyl ketone and 1- chloro-

3-methyl-2-butene, wherein the reaction is carried out in a 2-phase liquid system comprising an organic phase and an aqueous phase, in the presence of a phase transfer catalyst, said aqueous phase comprising an aqueous solution of an alkali metal hydroxide.

2. Process according to claim 1, in which 0.5 to 10 mol of diisopropyl ketone are employed per mole of 1-chloro-3-methyl-2-butene.

3. Process according to claim 1, in which the phase transfer catalyst is chosen from the group consisting of quaternary ammonium salts.

4. Process according to claim 1, in which 0.1 to 10 mol % of phase transfer catalyst, based on the starting compound employed in deficit, is employed.

5. Process according to claim 1, in which the reaction is carried out in the presence of an alkali metal hydroxide.

6. A tart-fresh perfume composition comprising 2,4,4,7-tetramethyl-oct-6-en-3-one.

* * * * *